United States Patent [19]

Wenteler et al.

[11] Patent Number: 4,956,502
[45] Date of Patent: Sep. 11, 1990

[54] PROCESS FOR THE PREPARATION OF ROOPEROL DERIVATIVE

[75] Inventors: George L. Wenteler, Pretoria; Karl H. Regel, Durban; Siegfried Drews, Pietermaritzburg; Hans Kundig, Witpoort, all of South Africa

[73] Assignee: Rooperol (N.A.) NV, Bonaire, Netherlands Antilles

[21] Appl. No.: 365,494

[22] Filed: Jun. 13, 1989

Related U.S. Application Data

[63] Continuation-in-part of Ser. No. 875,398, Jun. 17, 1986, abandoned.

[51] Int. Cl.$^5$ .................. C07C 39/205; C07C 39/21; C07C 33/28
[52] U.S. Cl. .................................. 568/729; 568/715; 568/716; 568/717; 568/763; 568/808; 568/813
[58] Field of Search ............... 568/729, 717, 763, 808, 568/813, 715, 716

[56] References Cited

U.S. PATENT DOCUMENTS 4,644,085  2/1987  Drewes et al. .................. 568/729

FOREIGN PATENT DOCUMENTS 206765  12/1986  European Pat. Off. .......... 568/729
2120650  12/1983  United Kingdom .............. 568/729

Primary Examiner—Werren B. Lone
Attorney, Agent, or Firm—Vidas & Arrett

[57] ABSTRACT

A process for preparing a compound of the formula

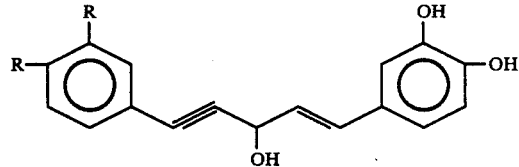

in which both Rs and H or OH; comprising the steps
a. of treating the ethyl ester of caffeic acid with trialkylsilyl chloride at ambient conditions in equimolar proportions in the presence of a base;
b. the reduction of the ester to the corresponding allylic alcohol with aluminum hydride reagent;
c. of oxidizing the resulting product with manganese dioxide at ambient temperature and in excess molar proportion to yield the corresponding allylic aldehyde;
d. of coupling the latter with the silyl ether of the relative phenyl acetylide; and
e. of hydrolysis of this coupled product with alkylammonium fluoride at ambient conditions in equimolar proportions.

1 Claim, No Drawings

PROCESS FOR THE PREPARATION OF ROOPEROL DERIVATIVE

REFERENCE TO RELATED CASES

This application is a continuation-in-part of Ser. No. 875,398 filed June 17, 1986, now abandoned, the disclosure of which is incorporated herein by reference. The application is also related to an application of the same inventors entitled PROCESS FOR THE PREPARATION OF ROOPEROL filed concurrently herewith as a continuation-in-part of Ser. No. 875,398.

FIELD OF THE INVENTION

The invention related to a process for the preparation of the 3-hydroxy derivative of Rooperol and related compounds.

BACKGROUND OF THE INVENTION

The isolation of E-1,5-bis(3,4-dihydroxyphenyl)pent-4-en-1-yne 4,4 di-β-D-glucopyranoside, Hypoxoside, from *Hypoxis obtusa* and *Hypoxis rooperi* has been described by Marini-Bettolo[1] and Drewes[2]. The use of Hypoxoside, Rooperol and related pent-4-en-1-yne derivatives, including the 3-hydroxy derivative, in anticancer compositions are disclosed (U.S. Pat. No. 4,644,085, European Patent No. 130,829). The preparation of Rooperol by the hydrolysis of Hypoxoside in water at a pH 6.3 with B-glucosidase at preferably 37° C., the preparation of the tetra-acetate from Rooperol by acylation with (Ac₂O/C₅H₅N), and also the preparation of tetramethoxy-rooperol from Rooperol by methylation with diazomethane has been disclosed[1,2]. The synthesis of the tetramethoxy derivative of Rooperol is achieved by the conversion of 3,4-dimethoxybenzaldehyde to the alkynide anion of 3,4-dimethoxyethynylbenzene (3 steps) and subsequent coupling to 3,4-dimethoxycinnamyl chloride obtained from 3-(3,4-dimethoxyphenyl)prop-2-enoic acid (3 steps) via copper catalysis. Similar synthetic sequences using phenyl rings with no substituents or precursors in which one or both phenyl rings carry methoxy- or methylenedioxy substituents, have been described[2]. Although a variety of protecting groups have been used, the removal of these protecting groups to yield Rooperol has been unsuccessful due to the highly reactive nature of the pent-4-en-1-yne system. It is the object of this invention to provide a process for the synthesis of the 3-hydroxy derivative of Rooperol, and related analogue compounds.

DESCRIPTION OF THE INVENTION

A process for preparing a compound of the formula:

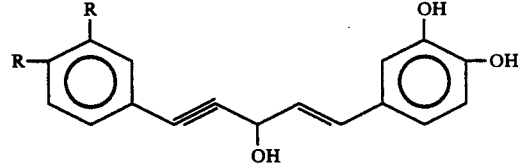

in which both Rs are H or OH. comprising the steps
a. of treating the ethyl ester of caffeic acid with trialkylsilyl chloride at ambient conditions in equimolar proportions in the presence of a base;
b. the reduction of the ester to the corresponding allylic alcohol with aluminium hydride reagent;
c. of oxidizing the resulting product with manganese dioxide at ambient temperature and in excess molar proportion to yield the corresponding allylic aldehyde;
d. of coupling the latter with the silyl ether of the relative phenyl acetylide; and
e. of hydrolysis of this coupled product with alkylammonium fluoride at ambient conditions in equimolar proportions.

The preparation of these 3-hydroxy derivatives is outlined in the following Scheme which shows the eseterification of caffeic acid, the silylation of the resulting ester, reduction to the allylic alcohol, the oxidation thereof with MnO₂ to yield an aldehyde (5) and then (a) reaction with anion of the silyl ether of the 3,4-dihydroxphenyl-ethyne, followed by deprotection of the silyl groups, or (b) reaction with phenylacetylide followed by deprotection of the silyl groups.

Scheme

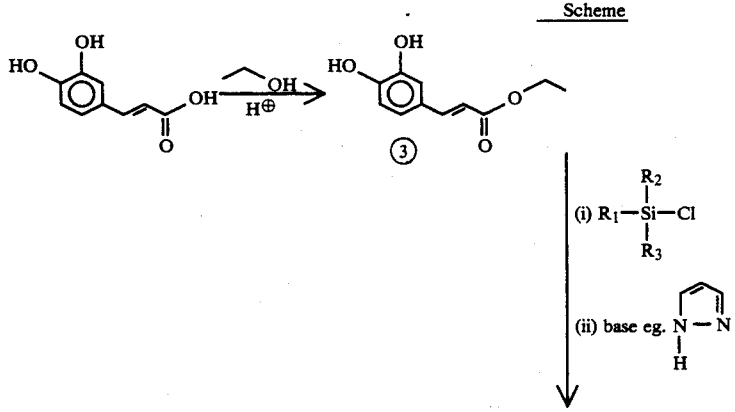

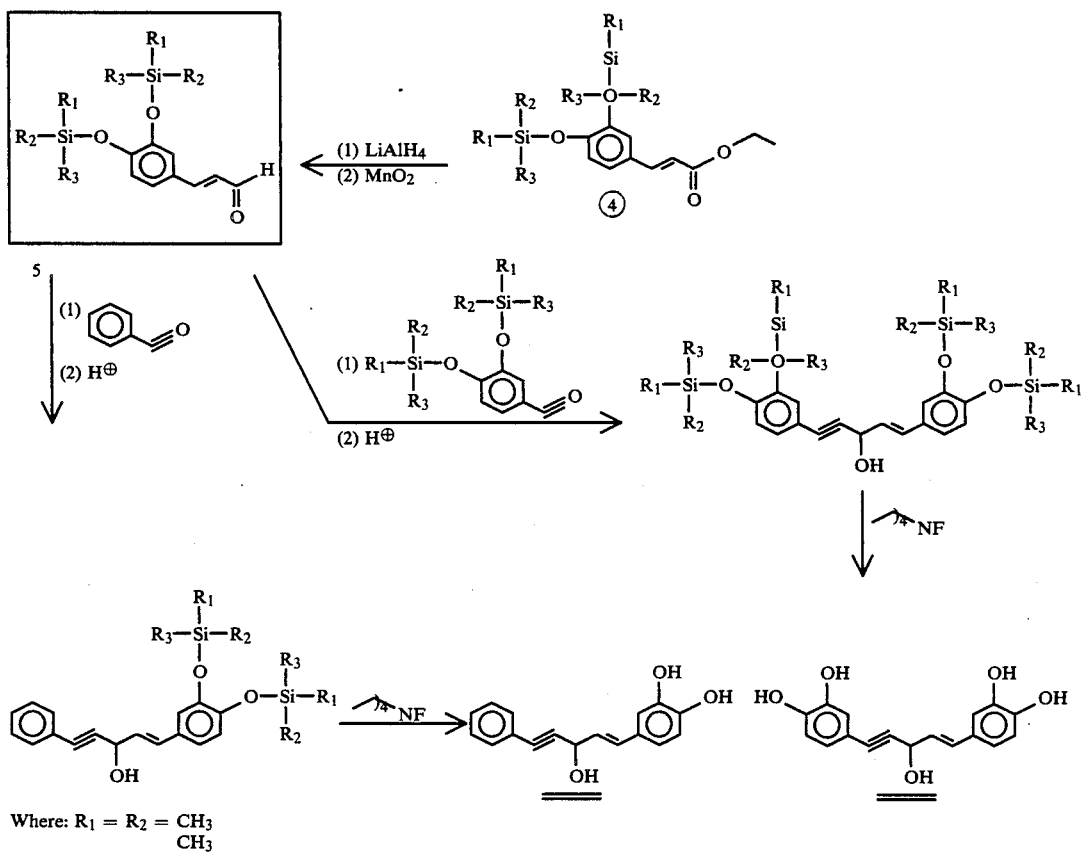

Where: $R_1 = R_2 = CH_3$
$CH_3$

PROCEDURES

I. Synthesis of the ethyl ester of caffeic acid (3,4-dehydroxycinannmic acid)

Method

A solution of caffeic acid (10.0 g, 0.055 mol) in a mixture of benzene (300 ml), ethanol (80 ml) and $H_2SO_4$ (conc. 5 ml) is refluxed for 34 hours. The cooled dark green reaction mixture is neutralized with a saturated aqueous $NaHCO_3$ solution. The aqueous layer is then extracted with ether (3×15 ml), dried ($MgSO_4$) and the combined organic extracts cncentrated to yield a brown crystalline product (9.0 g, 78%).

Recrystallization from ethyl acetate yielded the ethyl ester of caffeic acid as a light brown crystalline produce (5.98 g, 52%) mp 143°–146° C.; δH (acetone; 80 MHz; TMS): 1.27(3H, t, J=7.1 Hz, $CH_2CH_3$); 4.2(2H, t, J=7.1 Hz, $CH_2CH_3$), 6.27(1H, d, J=15.9 Hz, H-2) 6.82–7.18(3H, m, ArH), and 7.55(1H, d, J=15.9 Hz, H-3).

II. Protection of the aromatic OH groups as t-butyldimethylsilyl ethers

A solution of the ethyl ester of caffeic acid (1 eqv), t-butyldimethylchlorosilane (1.1 eqv per OH group), and imidazole (1.2 eqv) in DMF is stirred for 24 hours at 23° C. The solution is quenched with a saturated aqueous solution of $NaHCO_3$ and extracted with ether. The combined extracts are washed with water, dried ($MgSO_4$), which is purified by suitable methods to yield the disilyl ether of the ethyl ester of caffeic acid (compound 4 in the Scheme).

Compound 4

$\delta_H$(CDCl$_3$; 80 MHz, TMS): 0.25(12H, s, —Si—CH$_3$, 0.90(18H, s, Si+CH$_3$), 1.33(3H, t, J=7.08 Hz, $CH_2\underline{CH_3}$), 4.25(2H, q, J=7.08 Hz, $\underline{CH_2}$-CH$_3$), 6.22(1H, d, J=15.8 Hz, H-2); 6.75–7.06(3H, m, Ar$\underline{H}$) and 7.57(1H, d, J=15.8 Hz, H-3).

III. Synthesis of 3-[3,4-di(t-butyldimethylsiloxy)phenyl]prop-2-en-1-ol

Method

DIBAH (175 mg, 0.274 mmol) in toluene (3.3 ml) is added to a solution of the disilyl ether of the ester (4) (500 mg, 0.114 mmol) in toluene (1.5 ml) at −78° C. over a period of 1 hour. The reaction mixture is then allowed to reach room temperature when it is quenched with saturated aqueous NH$_4$Cl (10 ml) and extracted with ethyl acetate (3×10 ml). The combined extracts are dried (MgSO$_4$) and concentrated to provide a light yellow oil of 3-[3',4'-di(t-butyldimethylsiloxy)phenyl]-prop-2-en-1-ol (350 mg, 78%); $\delta_H$(CDCl$_3$; 80 MHz; TMS): 0.25(12H, s, Si—CH$_3$), 0.9(18H, s, Si+CH$_3$), 1.22–1.28(2H, m, $\underline{CH_2}$), 4.22(1H, d, J=5.1 Hz, H-2), 6.20(1H, d, J=5.1 Hz, H-3) and 6.69–6.85(3H, m Ar$\underline{H}$).

III. Synthesis of 3-[3',4'-di(t-butyldimethylsiloxy)phenyl]prop-2-enal

Method

MnO$_2$ (2.95 g; 0.034 mol) is added to a solution of 3-(3,4-t-butylidmethylsiloxy)phenylprop-2-en-1-ol (250 mg, 0.0064 mol) in CH$_2$Cl$_2$ (10 ml). The reaction mixture is stirred for 24 hours and a light yellow oil of 5 (22o mg, 76%) is obtained after filtration and evaporation of the solvent under reduced pressure.

δH(CDCl$_3$; 80 MHz; TMS): 0.23(12H, s, Si—CH$_3$), 0.9(18H, s, Si+CH$_3$), 6.52(1H, dd, J=7.6 Hz and J=16 Hz, H-2), 6.99-7.11 (3H. m, ArH), 7.36 (1H, d, J=16 Hz, H-3) and 9.46 (1H, d, J=7.6 Hz, CHO).

IV. Synthesis of 3,4-di(t-butyldimethylsiloxy)-2',2'-dibromostyrene

Method

A suspension of activated zinc (1.90 g, 0,029 mol, 2 eqv), triphenylphosphine (7.60 g, 0.0029 mol, 2 eqv) and carbon tetrabromide (9.60 g, 0.029 mol, 2 eqv) in dry CH$_2$Cl$_2$ (20 ml) is stirred for 30 hours under N$_2$. To this Wittig reagent is added 3,4-di(t-butyldimethylsiloxy)-benzaldehyde (5.50 g, 0.015 mol) and the mixture is stirred for 3 hours at room temperature before it is quenched with pentane (50 ml) and filtered. The residue is washed with CH$_2$Cl$_2$ (30 ml) and the organic solvents are evaporated to provide the dibromide as a yellow oil (5.08 g, 66%). δ$_H$(CDCl$_3$; 80 MHz, TMS): 0.25(12H, s, —Si—CH$_3$), 0.90(18H, s, Si+CH$_3$) and 6.82(1H, s, CH) and 7.20-7.33(3H, m, ArH).

V. Synthesis of 3,4-di(t-butyldimethylsiloxy)phenylethyne

Method

To a solution of 3,4-di(t-butyldimethylsiloxy)-2',2'-dibromostyrene (3.00 g, 0.006 mol) in dry tetrahydrofuran (10 ml) is added BuLi (2 eqv) at −78° C. over a period of 1 hour. The reaction mixture is allowed to reach room temperature when it is quenched with saturated aq. NaHCO$_3$ (20 ml), extracted with ethyl acetate (3×20 ml) and the combined extracts are dried (MgSO$_4$) before the solvent was evaporated under reduced pressure to provide the corresponding acetylenic product as a dark brown oil (1.8 g, 86%). δ$_H$(CDCl$_3$; 80 MHz, TMS): 0.25(12H, s, —Si—CH$_3$), 0.9(18H, s, Si—CH$_3$), 2.96(1H, s, CH), and 6.69-7.26(3H, m, ArH).

VI. Preparation of phenylacetylide magnesium bromide

Bromoethane (1 mol equiv) is added dropwise to a stirred mixture magnesium metal (1.05 mol equiv) and tetrahydrofuran under anhydrous conditions and a N$_2$ atmosphere. Once the exothermic reaction has subsided, the reaction mixture is refluxed for 10 minutes, cooled to 20° C. and phenylacetylene (1.05 mol equiv) dissolved in THF is added dropwise. Ethane is evolved during the formation of the phenylacetylide magnesium bromide. The mixture is then refluxed for 45 minutes and cooled to 20° C.

VII. Preparation of 3',4'-di(tert-butyldimethylsiloxy) phenylacetylide magnesium bromide Bromoethane (1 mol equiv) is added dropwise to a stirred mixture of magnesium metal (1.05 mol equiv) and etrahydrofuran under anhydrous conditions and a N$_2$ atmosphere. Once the exothermic reaction has subsided, the reaction mixture is refluxed for 10 minutes, cooled at 20° C. and the alkyne as prepared in V (1.05 mol equiv) dissolved in THF is added dropwise. Ethane is evolved during the formation of the corresponding phenylacetylide magnesium bromode. The mixture is then refluxed for 45 minutes and cooled to 20° C.

VIII. Reaction of the aldehyde of Procedure III

The phenylacetylide magnesium bromide containing reaction mixture as prepared by method VII/or VII is cooled to 0° C. and the aldehyde of Procedure III dissolved in THF is added dropwise maintaining the temperature between 0°-5° C. After all the aldehyde has been added the reaction mixture is stirred for a further 2.5 hours at 25° C. and then poured into a saturated aqueous solution of NH$_4$Cl followed by ether extraction and work-up to yield the corresponding pent-4-ene-1-yn-3-ol product. Compound 17 resulted δ$_H$(CDCl$_3$; 80 MHz, TMS): 0.25(12H, s, Si—CH$_3$), 0.9(18H, s, Si—CH$_3$), 5.19(1H, d, J=5.9 Hz, H-3), 6.24(1H, dd, J=5.9 Hz and J=15 Hz), 6.8(1H, d, J=15 Hz, H-5) and 7.2-7.6(8H, m, ArH).

IX. Reaction of the aldehyde of Example III with Lithium (3,4-di(-tert-butyldimethylsilyloxyphenyl)acetylide(13) or phenylacetylide A THF solution of the phenylacetylide magnesium bromide (13) as prepared by procedure VI or VII is cooled to 0° C. and the aldehyde in dry THF is added dropwise maintaining the temperature between 0°-5° C. After all aldehyde has been added the mixture is stirred for a further 2.5 hours at 25° C. and then poured into a saturated aqueous solution of NH$_4$Cl followed by extraction with ether and work-up to yield the corresponding pent-4-ene-1-yn-3-ol product, i.e. compound 17.4

X. Deprotection of the silyl ether products

To a solution of the silyl ether (7) (1 eqv) in dry THF is added tetraethyl ammonium fluoride (4.8 eqv) in dry THF over a period of 15 minutes and the resulting mixture is stirred for an additional 3 hours at 23° C. The cooled reaction mixture is diluted with water and extracted several times with ethyl acetate. Solvent removal from dried MgSO$_4$ of the combined extracts under reduced pressure provided a residue which was purified according to standard procedures to provide 3-hydroxy rooperol, or the corresponding -(3',4'-dehydroxylphenyl) compound. δ$_H$(CDCl$_3$; 80 MHz; TMS): 0.25 (24H, s, Si—CH$_3$), 0.9 (36H, s, Si+CH$_3$) 5,18 (1H, d, J=5,9 Hz, H-3), 6,24 (1H, dd, J=5,9 Hz, J=15 Hz, H$_4$) and 6,7H, m ArH and H-5).

What is claimed is:

1. A process for preparing a compound of the formula

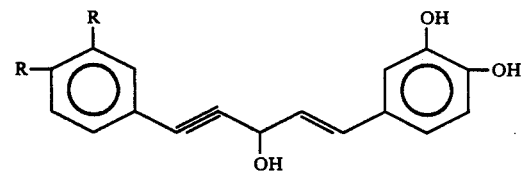

in which both Rs are H or OH comprising the steps
   a. of treating the ethyl ester of caffeic acid with trialkylsilyl chloride at ambient conditions in equimolar proportions in the presence of imidazole;

b. the reduction of the ester to the corresponding allylic alcohol with aluminium hydride reagent;

c. of oxidizing the resulting product with manganese dioxide at ambient temperature and in excess molar proportion to yield the corresponding allylic aldehyde;

d. of coupling the latter with the silyl ether of the relative phenyl acetylide; and e. of hydrolysis of this coupled product with alkylammonium fluoride at ambient conditions in equimolar proportions.

* * * * *